United States Patent
Hendriks et al.

(10) Patent No.: US 8,175,690 B2
(45) Date of Patent: May 8, 2012

(54) OPTICAL DEVICE FOR ASSESSING OPTICAL DEPTH IN A SAMPLE

(75) Inventors: Bernardus H. W. Hendriks, Eindhoven (NL); Antonius T. M. Van Gogh, S-Hertogenbosch (NL); Hans Zou, Windsor, NJ (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 335 days.

(21) Appl. No.: 12/527,727

(22) PCT Filed: Feb. 18, 2008

(86) PCT No.: PCT/IB2008/050575
§ 371 (c)(1),
(2), (4) Date: Aug. 19, 2009

(87) PCT Pub. No.: WO2008/102294
PCT Pub. Date: Aug. 28, 2008

(65) Prior Publication Data
US 2010/0113941 A1  May 6, 2010

Related U.S. Application Data

(60) Provisional application No. 60/890,695, filed on Feb. 20, 2007, provisional application No. 60/908,422, filed on Mar. 28, 2007.

(51) Int. Cl.
*A61B 6/00* (2006.01)
*A61B 6/08* (2006.01)
*G01J 4/00* (2006.01)
*G01J 3/447* (2006.01)
*G01N 21/47* (2006.01)

(52) U.S. Cl. .......... 600/478; 356/73; 356/364; 356/369; 250/559.09; 250/225

(58) Field of Classification Search .................. None
See application file for complete search history.

(56) References Cited

U.S. PATENT DOCUMENTS

| 5,847,394 | A | 12/1998 | Alfano et al. |
| 2003/0231309 | A1 | 12/2003 | Fulghum |
| 2005/0020893 | A1 | 1/2005 | Diab |
| 2006/0178570 | A1 | 8/2006 | Robinson et al. |

FOREIGN PATENT DOCUMENTS

| WO | 2000030530 A1 | 6/2000 |
| WO | 2001072216 A2 | 10/2001 |
| WO | 2005017495 A2 | 2/2005 |
| WO | 2005029051 A1 | 3/2005 |
| WO | 2005066614 A1 | 7/2005 |

OTHER PUBLICATIONS

Backman, Vadim et al "Polarized Light Scattering Sepctroscopy for Quantitative Measurement of Epithelial Cellular Structure in Situ" IEEE Journal of Selected Topics in Quantum Electronics, vol. 5, No. 4, Aug. 1999.

*Primary Examiner* — Long V. Le
*Assistant Examiner* — Farshad Negarestan

(57) ABSTRACT

An optical device for assessing optical depth in a sample illuminated by polarized radiation from a source include two radiation guides having their end portions arranged for capturing reflected radiation from the sample. A detector measures two polarizations of the reflected radiation, and two intensities of the reflected radiation in the two radiation guides, respectively. A processor is configured to calculate two pectral functions, which are indicative of single scattering events in the sample. The processor is further configured to calculate a measure of the correlation between the two spectral functions so as to assess whether the single scattering events originate from substantially the same optical depth within the sample. Thus, the causal relation between the two spectral functions can be used for assessing whether the single scattering events giving rise to the two spectral functions come from substantially the same optical depth within the sample.

20 Claims, 4 Drawing Sheets

OPTICAL DEVICE FOR ASSESSING OPTICAL DEPTH IN A SAMPLE

FIELD OF THE INVENTION

The present invention relates to an optical device for assessing optical depth in a sample. The invention also relates to a corresponding catheter, a corresponding method, and a corresponding computer program product.

BACKGROUND OF THE INVENTION

Optical characterization of a medical condition of a patient is currently an area of growth, partly due to the increasing number of possible medical conditions that are detectable by emerging optical technologies. In particular, early detection by optical methods of for example cancer may facilitate an opportunity for improved detection giving rising to an increased chance of survival for the patient. When medical relevant information is available from very small tissue volume, even pre-malignant changes in tissue morphology and physiology may become distinguishable.

More than 90% of all cancers are epithelial of origin. Body surfaces are mostly covered with a thin layer of epithelial tissue. This epithelial tissue layers of various organs have thickness ranging from less than 10 micron in simple (single layer) squamous epithelia to several hundred micron in stratified (multiple cell layers) epithelia. Below the epithelia layers various other tissue layers are present such as connective tissue, inflammatory cells, neurovascular structures etc. Since the penetration depth of light is, in general, much larger than that of the epithelial layer the backscattered light from the tissue contains information of the change in the epithelial layers superimposed on a large background signal arising form the deeper layered tissues. This makes it difficult to extract the relevant information from this signal directly. To solve this problem a method is needed in which the signal from the epithelial layer can be disentangled from the signal due to the deeper layers i.e. the background signal.

V. Backman et al. disclosed a solution to this problem in IEEE J. Selected Topics Quantum Electron., Vol. 5, No 4, July/August 1999, p. 1019. In the method by Backman et al., polarized light is used to illuminate the tissue. Thereafter, they detect the scattered light having the same polarization and the orthogonal polarization separately by using a polarizing beam splitter and two separate detectors. Since the signal coming from the epithelial layer will be scattered typically only once the polarization will be significantly preserved. The scattered light coming from the deeper layers, being multiple scattered, will loose the original polarization information and will become isotropically distributed whereby the original polarization is lost. By subtracting both signals from each other one can remove the background signal from the desired signal being backscattered from the epithelial layer.

A drawback of the method of Backman et al. is that there will normally still be single scattered photons coming from the layer deeper than the epithelial layer, these deeper layer may thus negatively influence the desired signal. Furthermore, because a large background signal is removed from the smaller actual signal, a significant amount of noise will be present in the final signal, which limits the measurement accuracy. This in turn limits the detection limit with regard to how early a cancer in the tissue can be detected. Additionally, if a patient is under temporal influence of a substance, e.g. a pharmaceutical drug, the optical properties of the epithelial layers may change in response to the said substance, thereby making the reliability of an optical assessment of a patient with this method even lower.

Hence, an improved optical device would be advantageous, and in particular a more efficient and/or reliable optical device would be advantageous.

SUMMARY OF THE INVENTION

Accordingly, the invention preferably seeks to mitigate, alleviate or eliminate one or more of the above mentioned disadvantages singly or in any combination. In particular, it may be seen as an object of the present invention to provide an optical device that solves the above mentioned problems of the prior art with obtaining a reliable signal from an optically thin layer.

This object and several other objects are obtained in a first aspect of the invention by providing an optical device for assessing optical depth in an associated sample, the device comprising:

a radiation source capable of emitting radiation with an initial polarization ($P\_0$), a first and a second radiation guide, the first radiation guide being optically connected to the radiation source for emitting radiation to the sample, the first and the second radiation guide having their respective end portions substantially aligned with each other, the end portions further being arranged for capturing reflected radiation from the sample, a detector being optically connected to the first and the second radiation guide, the detector being arranged for measuring, within an optical subband, an indication of:

a first polarization ($P\_1$) of the reflected radiation, a second polarization ($P\_2$) of the reflected radiation, said second polarization ($P\_2$) being different from the first polarization ($P\_1$), and a first and a second intensity ($I\_1$, $I\_2$) of the reflected radiation in the first and the second radiation guide, respectively, and processing means operably connected to the detector, the processing means being adapted to calculate a first (f) and a second (g) spectral function within the optical subband, both spectral functions (f, g) being substantially indicative of single scattering events in the sample:

the first spectral function (f) being a measure of the difference in polarization between the first ($P\_1$) polarization of the reflected radiation and the second ($P\_2$) polarization of the reflected radiation, and the second spectral function (g) being a measure of the difference in intensity between the first and second intensities ($I\_1$, $I\_2$) of the reflected radiation, wherein the processing means is further arranged to calculate a measure of the correlation between the first (f) and a second (g) spectral function so as to assess whether the single scattering events originate from substantially the same optical depth within the sample.

The invention is particularly, but not exclusively, advantageous for obtaining an optical device where the causal relation between the first and second spectral functions can be used for assessing whether the single scattering events giving rise to the two spectral functions, within the said optical subband, come from substantially the same optical depth (D) within the sample i.e. if there is a significant correlation (C) between the first (f) and the second (g) spectral function. For optical probing of e.g. an epithelial layer, the discrimination against the layers below the epithelial layer provides the advantage that correlation can be used as an indication of a reliable signal from the epithelial layer itself. In particular, for assessment of a medical condition of a patient, e.g. (pre)malignant lesions, this correlation can be the difference between providing information that may subsequently result in a correct diagnosis or providing information that may subsequently result in an incorrect diagnosis, the latter being for example either a false positive diagnosis or a false negative diagnosis.

The invention relies, in particular, on the fact that the underlying physical effect of both spectral functions is essentially independent of each other at least for many practical conditions and applications, in particular for medical applications. The depolarization of the sample resulting in the first spectral function (f) depends strongly on the type of molecules present, while the mean free path of the photon in the sample resulting in the second spectral function (g) depends strongly on the distribution of the molecules in the sample.

Thus, if both the first and second spectral functions are valid in the sense that they predominately originate from single scattering events, although obtained in different ways, the first and second spectral function should result in substantially the same spectral signal if appropriate correction is performed, e.g. normalization. There can be a significant correlation if e.g. there is a strong depolarisation in the sample and also the mean free path of the photons is larger than a characteristic diameter of the first and second radiation guides.

Hence, for the case of medical applications, if there is a strong correlation between the first and second spectral functions then the information provided may be used with better confidence in connection with a later diagnose. In case of a weak correlation, the parameter and/or conditions of the present invention may be modified or adapted, or alternatively, another method may be used to provide information for medical purposes.

In the context of the present invention, it is to be understood that the first (f) and the second (g) spectral functions are substantially indicative of single scattering events in the sense that predominately single scattering events in the sample contribute to the first and second spectral function. Nevertheless, there may also be a gradually dismissing contribution from double scattering events, triple scattering events, etc. to the first and/or the second spectral function, the contribution of these higher order scattering events depends in general on the specific interaction on the radiation and the optical properties as it will be readily appreciated by the skilled person once the general principle of the present invention is acknowledged. More specifically, the interaction and thereby the contribution from the higher order scattering events depends on the radiation type (e.g. monochromatic, broadband), the polarization of the radiation (linear, elliptic, circular), the intensity of the radiation (high power, low power), and of course on the optical scattering properties of the sample in question (absorption, elastic scattering, inelastic scattering, etc.). In general, the present invention relates to an inverse scattering problem, where the optical radiation reflected from the sample is used for extracting information about the sample. For more technical details, the reader is referred to Biomedical Photonics Handbook, Editor-in-CHief Tuan Vo-Dinh, CRC Press LLC, Florida, ISBN 0-8493-1116-0, see for instance chapter 2.

Though, the present invention may find appropriate applications in the medical field, the teaching of the invention is not limited to this technical field. Rather, the invention may find also application in many optical applications and areas, where an optically response from an optically thin layer superposed on some kind of substrate is desired, the condition being that the optically thin layer should preferably not be conducting e.g. metallic, because conducting layers in general have a much higher reflectance i.e. the deeper layers will usually not be probed by an impinging beam of radiation. Therefore other applications are envisioned where the surface of a biological sample is to be analysed. Alternatively, semi-conducting surface layers, e.g. silicon or modifications thereof like silica, may be analysed by the present invention.

Beneficially, the first spectral function (f) may be a polarized light scattering spectroscopy (PLSS) function. Additionally or alternatively, the second spectral function (g) may be a measure of the differential path length (DPL) between the first and the second radiation guide.

Typically, the detector may be arranged for measuring, within the optical subband, the first polarization ($P\_1$) and the second polarization ($P\_2$) of the reflected radiation captured by the first radiation guide to provide the simplest optical path for the polarized radiation. However, the detector may alternative or additionally be arranged for measuring, within the optical subband, the first polarization ($P\_1$) and the second polarization ($P\_2$) of the reflected radiation captured by the second radiation guide.

In an embodiment, an additional third radiation guide may be arranged for transmitting radiation with the initial polarization ($P\_0$) to the sample, the third radiation guide having an end portion substantially aligned with the end portions of the first and the second radiation guide. This embodiment however requires additional space for the third radiation guide. Usually, the third radiation guide may be arranged for capturing reflected radiation from the sample, the third radiation guide being optically connected to the detector. In particular, this third radiation guide provides the advantage that the PLSS and DPL measurements can be performed in separate radiation guides in parallel with each other.

In another embodiment, the detector may be arranged for measuring the first ($P\_1$) and the second ($P\_2$) polarization of the reflected radiation in two substantially orthogonal directions. Thus, if the relative orientation of the measured polarizations is orthogonal, one typically obtains the maximum differential signal. Additionally or alternatively, the radiation source may be arranged for emitting radiation having the initial polarization ($P\_0$) linearly polarized in a plane substantially parallel to a polarization plane of the measured first ($P\_1$) or the measured second ($P\_2$) polarization in order to provide a simple, yet effective optical configuration of the optical device. It may, in some applications, be more advantageous to apply circularly polarized radiation as this polarization is better conserved in some kind of radiation guides.

In one embodiment, the first, the second and/or the third radiation guide may be optical fibres. The optical fibres may have a diameter (disregarding cladding) of maximum 200 micrometer, preferably maximum 100 micrometer, or even more preferably maximum 50 micrometer.

However, in connection with the embodiment, where the third radiation guide may be arranged for capturing reflected radiation from the sample in order to perform polarised light scattering spectroscopy (PLSS) therewith, the third radiation guide may then have a maximum diameter of 100 micrometer, preferably maximum 50 micrometer, or even more preferably maximum 25 micrometer, because, in general, the smaller the diameter of the radiation guide, the better the polarization is preserved through the radiation guide.

Similarly, in connection with said embodiment of the third radiation guide, the first and/or second radiation guide may then have a minimum diameter of 100 micrometer, preferably minimum 200 micrometer, even more preferably minimum 300 micrometer, or most preferred 400 micrometer in order to perform differential path length (DPL) spectroscopy, because, in general, the diameter of the radiation guides sets the upper limit for how far one can penetrate into a sample with DPL.

In another embodiment, the processing means may be further arranged for determining the correlation for more than one region within the optical subband, the processing means may then be adapted to subsequently select a region of optimum correlation (C) for subsequent optical measurements in order to choose an optimum setting for e.g. a subsequent measurement of a medical condition of a patient. Alternatively or additionally, the processing means may be further arranged for changing the optical subband in dependency on the found correlation.

Beneficially, the optical device may comprise actuation means arranged for changing at least the distance of the respective end portions between the first and second radiation guide in dependency of the correlation. Possibly, the actuation means could also adjust their relative position in relation to one another and/or the sample.

In one embodiment, the first, the second and/or the third radiation guide may form part of a catheter, the catheter being suitable for in-vivo characterization of a patient.

In a second aspect, the present invention relates to a catheter arranged for cooperation with an associated optical device, the catheter comprising:
a first and a second radiation guide, the first radiation guide being optically connectable to an radiation source for emitting radiation to a sample, the first and the second radiation guide having their respective end portions substantially aligned with each other, the end portions further being arranged for capturing reflected radiation from the sample,
the associated optical device comprising:
a radiation source capable of emitting radiation with an initial polarization (P_0),
a detector being optically connected to the first and the second radiation guide, the detector being arranged for measuring, within an optical subband, an indication of:
  a first polarization (P_1) of the reflected radiation,
  a second polarization (P_2) of the reflected radiation, said second polarization (P_2) being different from the first polarization (P_1), and
  a first and a second intensity (I_1, I_2) of the reflected radiation in the first and the second radiation guide, respectively, and
processing means operably connected to the detector, the processing means being adapted to calculate a first (f) and a second (g) spectral function within the optical subband, both spectral functions (f, g) being substantially indicative of single scattering events in the sample:
  the first spectral function (f) being a measure of the difference in polarization between the first (P_1) polarization of the reflected radiation and the second (P_2) polarization of the reflected radiation, and
  the second spectral function (g) being a measure of the difference in intensity between the first and second intensities (I_1, I_2) of the reflected radiation,
the processing means further being arranged to calculate a measure of the correlation between the first (f) and a second (g) spectral function so as to assess whether the single scattering events originate from substantially the same optical depth within the sample.

Advantageously, within the catheter a third radiation guide may be arranged for transmitting radiation with the initial polarization (P_0) to the sample, the third radiation guide having an end portion substantially aligned with the end portions of the first and the second radiation guide. The third radiation guide may then be arranged for capturing reflected radiation from the sample, the third radiation guide being also optically connectable to the detector in order to perform polarised light scattering spectroscopy (PLSS). In particular, the third radiation guide provides the advantage that the PLSS and the differential path length (DPL) spectroscopy measurements can be performed in separate radiation guides in parallel with each other. Thereby, the invention can mitigate the opposing requirement with respect to the diameter of the radiation guides between PLSS, where a lower diameter of the radiation guide is typically desired, and DPL, where a higher diameter of the radiation guide is usually wanted.

Beneficially the first, the second and/or the third radiation guide may have polarization conserving properties so as to facilitate substantially undistorted measurement of the first (P_1) and second (P_2) polarization.

In third aspect, the present invention relates to a method for operating an optical device for assessing optical depth (D) in a sample, the method comprising:
emitting radiation with an initial polarization (P_0) with a radiation source, arranging a first and a second radiation guide in relation to the sample, the first radiation guide being optically connected to the radiation source for emitting radiation to the sample, the first and the second radiation guide having their respective end portions substantially aligned with each other, the end portions further being arranged for capturing reflected radiation from the sample,
providing a detector in optical connection to the first and the second radiation guide, the detector being arranged for measuring, within an optical subband, an indication of:
  a first polarization (P_1) of the reflected radiation,
  a second polarization (P_2) of the reflected radiation, said second polarization (P_2) being different from the first polarization (P_1), and
  a first and a second intensity (I_1, I_2) of the reflected radiation in the first and the second radiation guide, respectively, and
providing processing means operably connected to the detector, the processing means being adapted to calculate a first (f) and a second (g) spectral function within the optical subband, both spectral functions (f, g) being substantially indicative of single scattering events in the sample:
  the first spectral function (f) being a measure of the difference in polarization between the first (P_1) polarization of the reflected radiation and the second (P_2) polarization of the reflected radiation, and
  the second spectral function (g) being a measure of the difference in intensity between the first and second intensities (I_1, I_2) of the reflected radiation,
calculating by the processing means a measure of the correlation between the first (f) and a second (g) spectral function so as to assess whether the single scattering events originate from substantially the same optical depth within the sample.

In a fourth aspect, the invention relates to a computer program product being adapted to enable a computer system comprising at least one computer having data storage means associated therewith to control an optical device according to the third aspect of the invention.

This aspect of the invention is particularly, but not exclusively, advantageous in that the present invention may be implemented by a computer program product enabling a computer system to perform the operations of the second aspect of the invention. Thus, it is contemplated that some known optical device may be changed to operate according to the present invention by installing a computer program product on a computer system controlling the said known optical device. Such a computer program product may be provided on any kind of computer readable medium, e.g. magnetically or optically based medium, or through a computer based network, e.g. the Internet.

The first, second, third and fourth aspect of the present invention may each be combined with any of the other aspects. These and other aspects of the invention will be apparent from and elucidated with reference to the embodiments described hereinafter.

BRIEF DESCRIPTION OF THE FIGURES

The present invention will now be explained, by way of example only, with reference to the accompanying Figures, where.

DETAILED DESCRIPTION OF AN EMBODIMENT

Figure 1:
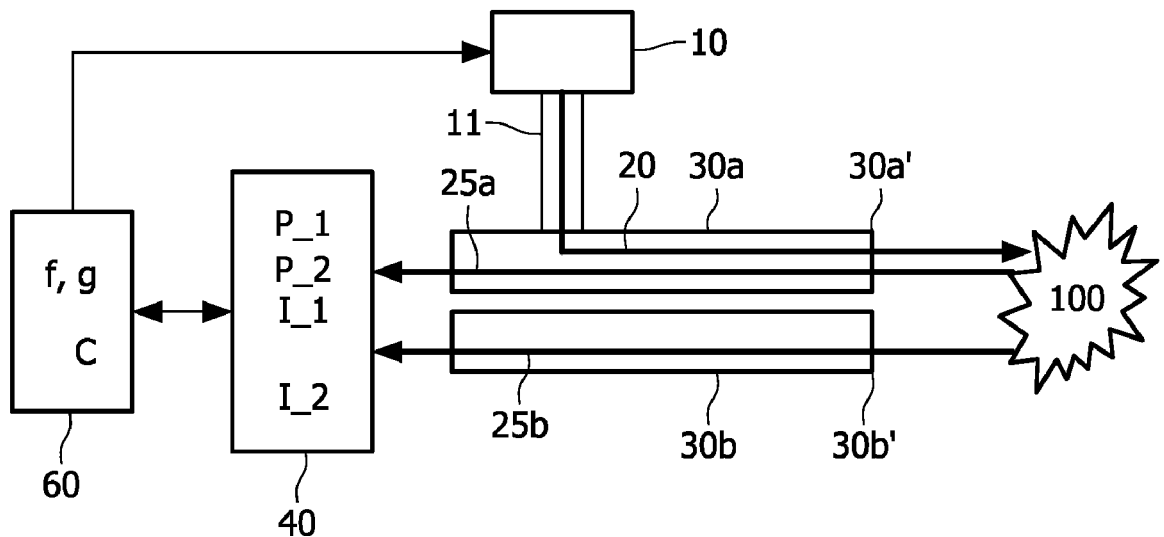
FIG. 1 is a schematic drawing of an optical device according to the invention.

FIG. 1 is a schematic drawing of an optical device that can be used for assessing optical depth D, cf. FIGS. 3 and 4 below, in an associated sample 100. The optical device comprises a radiation source 10 capable of emitting radiation 20 with an initial polarization P_0. The radiation source 10 can for instance be a conventional laser or a tungsten lamp with a suitable polarization filter optically connected thereto at any position along the optical path towards the sample. By the term "radiation", it is to be understood that any kind of suitable radiation can be applied in the context of the present invention, e.g. infra reed (IR) light, visible light, ultraviolet (UV) light, and (soft) X-radiation can be applied.

Additionally, a first 30a and a second 30b radiation guide are comprised in the optical device, the first and second radiation guide may e.g. be optical fibres or other suitable optical guiding means. The first radiation guide 30a is optically connected to the radiation source 10 for emitting radiation 20 to the sample 100 as indicated in FIG. 1, the first radiation guide 30a having a substantially polarization preserving property. The radiation source 10 can be optically connected to the first radiation guide 30a by an auxiliary radiation guide 11.

As schematically indicated in FIG. 1, the first and the second radiation guide have their respective end portions 30a' and 30b' substantially aligned with each other, the end portions further being arranged for capturing reflected radiation 25a and 25b from the sample 100. With this optical configuration of the first and second radiation guide it is possible to perform differential path length spectroscopy (DPL) with the optical device according to the invention. For further details about DPL, the reader is referred to WO 2005/029051 (Amelink and Sterenborg), which is hereby incorporated by reference in its entirety.

The optical device also comprises a detector 40, which is optically connected to the first 30a and the second 30b radiation guide. The detector 40 is arranged for measuring, within an optical subband, an indication of:
  a first polarization P_1 of the reflected radiation 25,
  a second polarization P_2 of the reflected radiation 25, said second polarization P_2 being different from the first polarization P_1, and
  a first I_1 and a second intensity I_2 of the reflected radiation 25a and 25b in the first 30a and the second 30b radiation guide, respectively.

The detector 40 can for instance be one or more spectrometers with appropriate polarization detection means, e.g. polarization filters or corresponding optical units. Thus, the measured first I_1 and the second intensity I_2 can be spectrographs of a certain radiation band as defined by the said optical subband. By detecting the first polarization P_1 and the second polarization P_2 of the reflected radiation 25, said second polarization P_2 being different from the first polarization P_1, it is possible to perform polarization light scattering spectroscopy (PLSS) with to the optical device. For further details about PLSS, the reader is referred to V. Backman et al. in IEEE J. Selected Topics Quantum Electron., Vol. 5, No 4, July/August 1999, p. 1019, which is hereby incorporated by reference in its entirety.

Additionally, processing means 60 are operably connected to the detector 40, the processing means being adapted to calculate a first (f) and a second (g) spectral function within the optical subband, both spectral functions (f, g) being substantially indicative of single scattering events in the sample. Nevertheless, there can also be a gradually dismissing contribution from double scattering events, triple scattering events, etc. to the first (f) and/or the second (g) spectral function as explained above. The processing means can be implemented as computer software running on one or more data processors and/or digital signal processors as would be readily realized by the skilled person.

The first spectral function (f) is a measure of the difference in polarization between the first P_1 polarization of the reflected radiation 25 and the second P_2 polarization of the reflected radiation 25. As indicated in FIG. 1 by the relative position of P_1 and P_2, the first and second polarization can be detected from the reflected light 25a being captured by the first radiation guide 25a, but alternatively or additionally the first and second polarization can be detected from the reflected light 25b being captured by the second radiation guide 25b (not shown in FIG. 1).

The second spectral function (g) is a measure of the difference in intensity between the first I_1 and second I_2 intensities of the reflected radiation in the first 25a and second 25b beam of radiation.

The processing means 60 is further arranged to calculate a measure of the correlation (C) between the first (f) and a second (g) spectral function so as to assess whether the single scattering events originate from substantially the same optical depth (D) within the sample 100.

Figure 2:
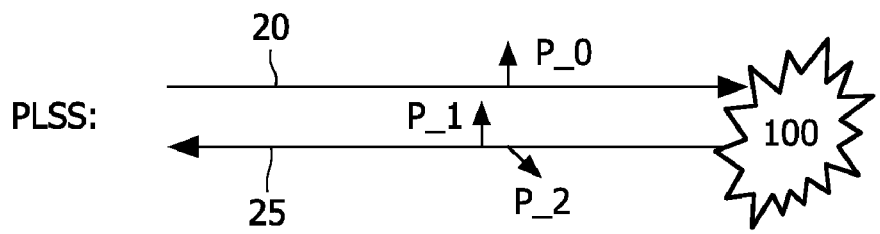
FIG. 2 is a schematic drawing of the optical paths for PLSS and DPL.
Figure 2:
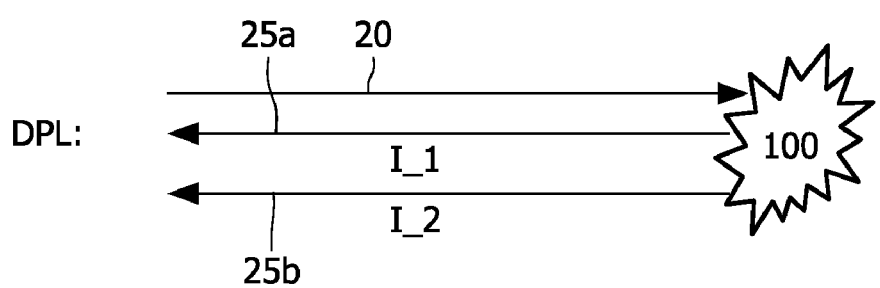

FIG. 2 is a schematic drawing of the optical paths for PLSS (upper part) and DPL (lower part).

For PLSS, the initial polarization of the incident light 20 is indicated by P_0. Upon backscattering the reflected light 25 will have a characteristic polarization having at least two components P_1 and P_2, which the detector 40 (not shown in FIG. 2) is arranged for measuring. The first P_1 and the second P_2 polarization of the reflected radiation 25 are indicated as pointing in two substantially orthogonal directions as this may advantageously result in the maximal difference between the two measured polarization directions, though other relative orientations are also possible. Typically, the radiation source 10 (e.g. a solid state laser) emits radiation with the initial polarization P_0 being linearly polarized in a plane substantially parallel to a polarization plane of the measured first polarization P_1 (as shown in FIG. 2) or the measured second P_2 polarization.

For DPL, the intensity difference between the first I_1 and the second intensity I_2 of the reflected radiation 25a and 25b, respectively, is applied for further analysis. The relative position of the first and second radiation guide 30a and 30b (not shown) is of course quite important with respect to what kind of information will obtained from the differential signal of the intensities. Likewise, the effective diameter of the radiation guides, e.g. the optical fibres, is of high importance for DPL spectroscopy. As a rule of thumb, the diameter of the optical fibre is approximately twice of the probing depth into the tissue for DPL.

Figure 3:
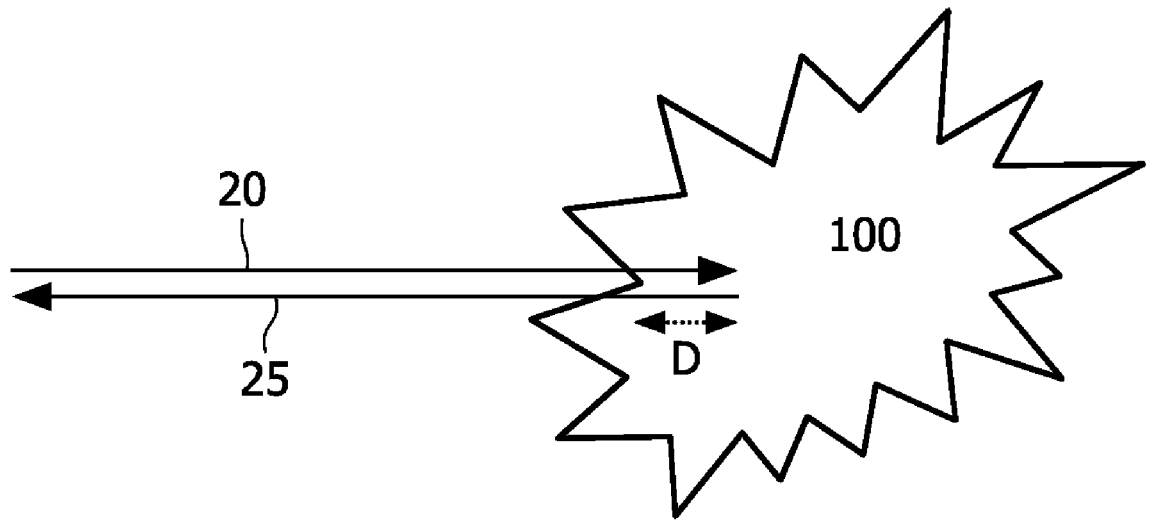
FIG. 3 is a schematic drawing of the optical path within the associated sample for single scattering events.

FIG. 3 is a schematic drawing of the optical path within the associated sample 100 for single scattering events. As indicated in FIG. 3, the incident radiation 20 penetrates into the sample 100 with a certain optical depth D and upon optical interaction at a site within the sample 100 there is reflected radiation 25 in a certain direction. In order to measure the reflected radiation 25 with the optical device it is usually necessary, as indicated in FIG. 3, that the reflected radiation 25 is approximately or exactly backscattered along the direction of the incident radiation 20. However, by lenses and/or broader diameter of the radiation guides 30, the solid angle of capture for reflected radiation 25 can be increased.

Figure 4:
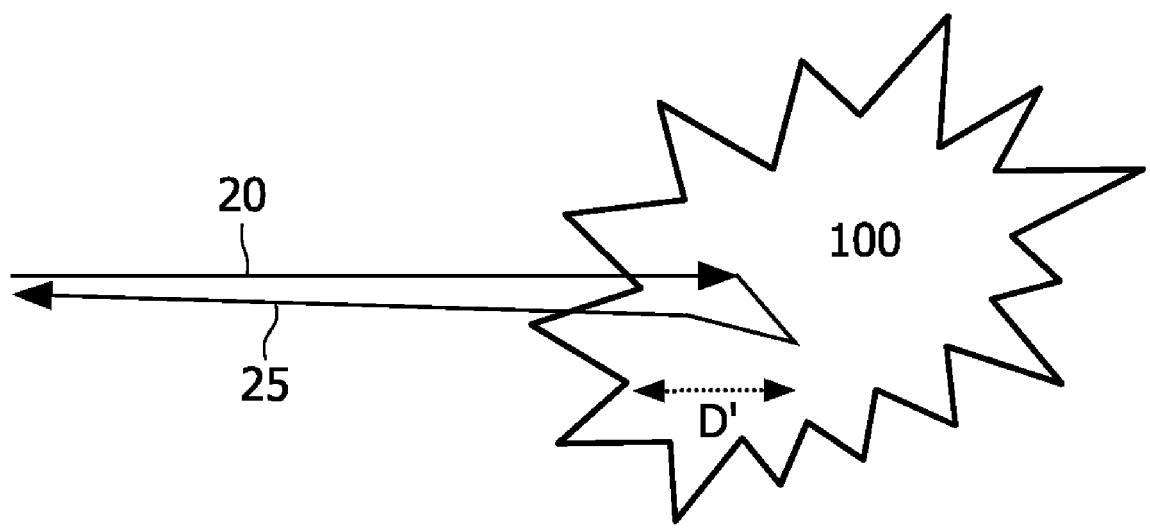
FIG. 4 is a schematic drawing of the optical path within the associated sample for multiple scattering events, FIG. 5 schematically shows a graph with the first (f) and the second (g) spectral function and two examples of the calculated correlation (C) thereof.

FIG. 4 is a schematic drawing of the optical path within the associated sample 100 for multiple scattering events. Similarly to FIG. 3, the incident radiation 20 is scattered at a site within the sample 100 and subsequently the reflected radiation 25 is scattered twice within the sample 100 as indicated by the two breaks in the arrow 25 marking the optical path of the reflected radiation 25. The detected radiation 25 has therefore penetrated into an optical depth D', and the reflected radiation 25 accordingly contains information about the sample within this depth, the information being a summarized contribution of the three scattering events, and it is hardly possible to disentangle the individual contribution from each scattering event.

Figure 5:
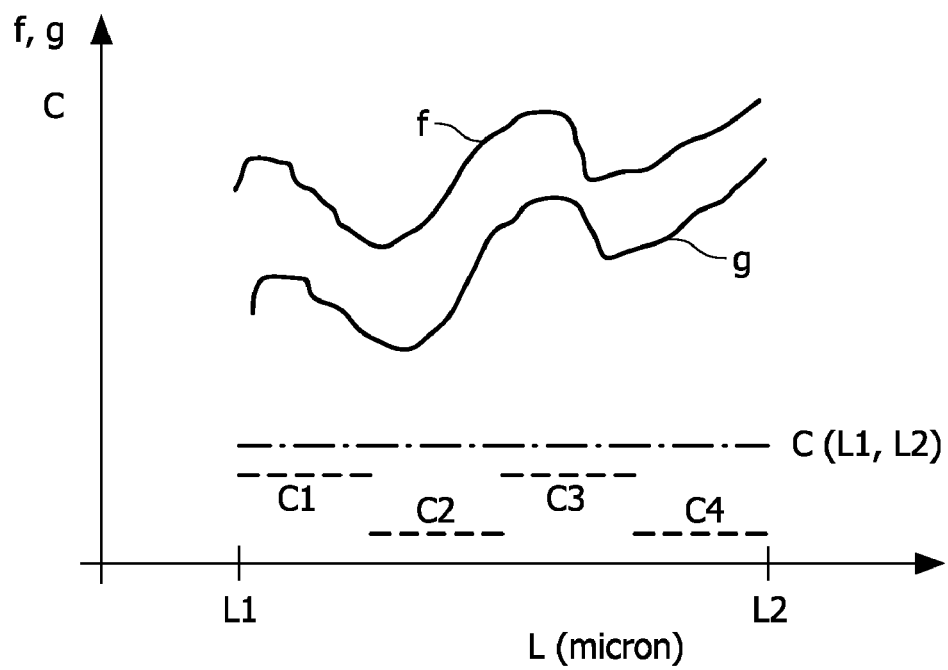

FIG. 5 schematically shows a graph with the first (f) and the second (g) spectral function on along the vertical axis and the wavelength (L, in micrometer) along the horizontal axis. The two spectral functions are shown within the optical subband from L1 to L2.

The correlation C between the first (f) and the second (g) spectral function can be calculated with normalisation as follows:

$$C(L1, L2) = \int_{L1}^{L2} \left| \frac{g(L)}{g_0} - \frac{f(L)}{f_0} \right| dL, \quad (1)$$

$$g_0 = \int_{L1}^{L2} g(L) dL$$

$$f_0 = \int_{L1}^{L2} f(L) dL$$

Thus, when there is a high correlation, C is equal or close to zero, and if the correlation is low, C is approximately two for most spectras. Other methods of calculating the correlation C is readily available to the skilled person.

Below the two spectral functions in FIG. 5, the calculated correlation C (L1, L2) is shown as a constant. The correlation C (L1, L2) can be compared to predetermined values defining acceptable levels of confidence that the scattering events resulting in the two spectral functions (f,g) originate from the same optical depth D within the sample 100. If the level of correlation is not acceptable as compared to the predetermined values, the processing means 60 can adjust the optical subband L1, L2 of the detector 40, change the radiation 20 of the radiation source 10 (power, wavelength, repetition frequency, etc.), modify the relative position of the first 25a and second 25b radiation guide, suggest changing of diameter of the first 25a and/or second 25b radiation guide and/or change settings of the detector 40 (sampling rate, sensitivity, etc.). The processing means 60 can be arranged to initiate these changes or modifications without the approval of an operator controlling the optical device, or the processing means can ask for approval of the operator, possibly the processing means can suggest some of the modifications to the operator e.g. changing the diameter of the radiation guides by using another set of radiation guides.

Alternatively, the correlation C can be calculated by the processing means 60 in more than one region within the optical subband as indicated by the four correlations C1, C2, C3, and C4. The four regions are shown as non-overlapping for clarity, but the regions may also overlap with one another. The processing means can subsequently select a region of optimum correlation (C) for subsequent optical measurements with the optical device, in particular optimum correlation (C) for purposes of later diagnosis can be selected.

In another embodiment, the processing means 60 can add together the correlations from the more than one region (e.g. four as in FIG. 5) within the optical subband L1, L2 in order to obtain an overall value of correlation C. Possible, the correlations can be summed together with specific weights for each correlations, the weight being decided upon by the specific correlation found (e.g. C1, C2, etc.), a pre-determined spectral characteristics (e.g. an upper or lower value of f), and/or the spectral region (wavelength L).

Figure 6:
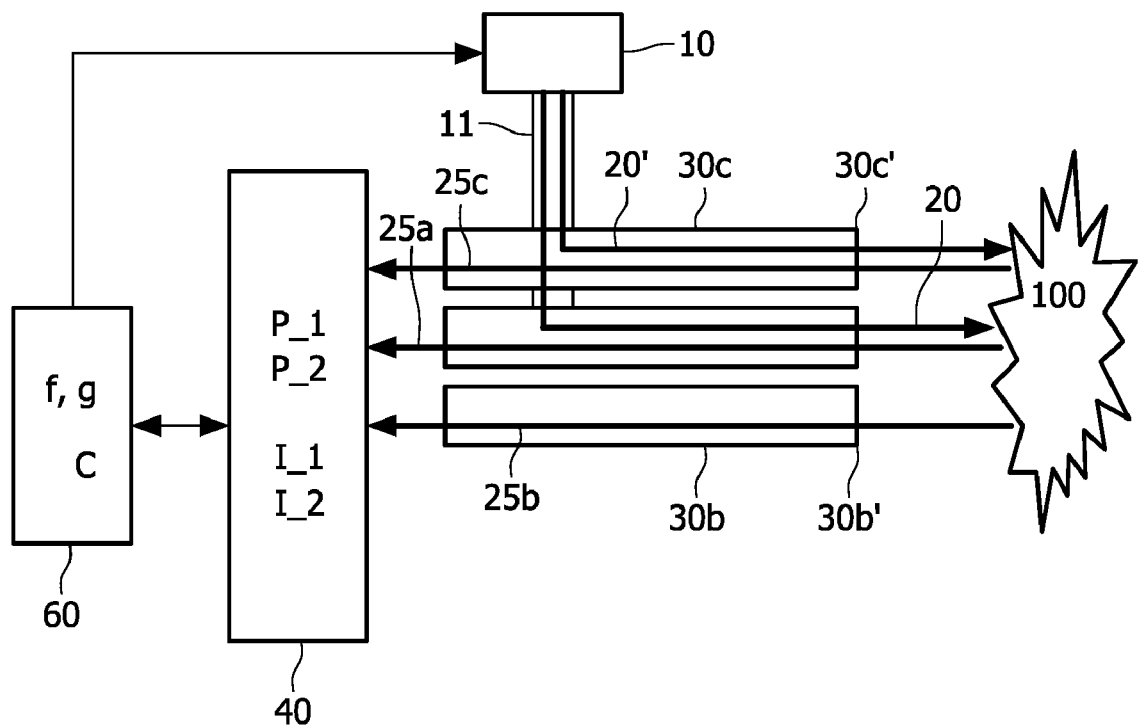
FIG. 6 is a schematic drawing of an alternative optical device according to the invention.

FIG. 6 is a schematic drawing of an alternative optical device according to the invention, wherein a third radiation guide 30c is arranged for transmitting radiation 20' with the initial polarization P_0 to the sample 100. The optical device shown in FIG. 6 is otherwise similar to optical device shown in FIG. 1. The third radiation guide 30c may also have an end portion 30c' substantially aligned with the end portions 30a' and 30b' of the first and the second radiation guide, respectively. Parallel to the radiation 20' through the third radiation guide 25a, the first radiation guide transmits radiation 20 to the sample 100, the radiation 20 does not necessarily need a polarization because the PLSS can be performed exclusively in the additional third radiation guide 30c by using the reflected light 25c as indicated in FIG. 6. In this embodiment, the radiation source 10 can also be divided into two separate and mutually independent radiation sources (not shown in FIG. 6). This embodiment of the optical device has the advantage that the PLSS and DPL can then be performed independent of each other, thereby making it possible to design the optical device without the constraint that the first 30a and/or the second 30b radiation guides have to be able to perform both kind of spectroscopy.

Figure 7:
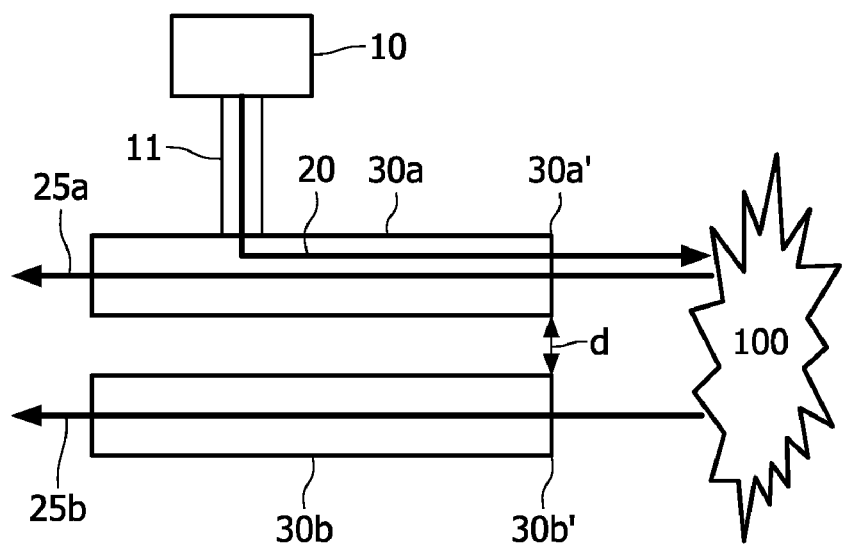
FIG. 7 is a schematic drawing of an alternative optical device according to the invention.

FIG. 7 is a schematic drawing of an alternative optical device comprising actuation means (not shown) arranged for changing the distance d (indicated by the double arrow) of the respective end portions 30a' and 30b' between the first 30a and second 30b radiation guide in dependency of the correlation C. Thus, the correlation C can be optimised as a function of the distance d. The first and second spectral function can usually be quickly found (less than a fraction of a second)

by currently available optical equipment and similarly the correlation C can found even faster by conventional computation means, which means that even if the optical device is applied on a patient there is often time for performing such an optimization of the correlation and the radiation guide distance d. Thus, in-vivo characterisation by the optical device according to the invention is feasible. The optical device shown in FIG. 7 is otherwise similar to optical device shown in FIG. 1, the detector 40 and processing means 60 being omitted for clarity.

Figure 8:
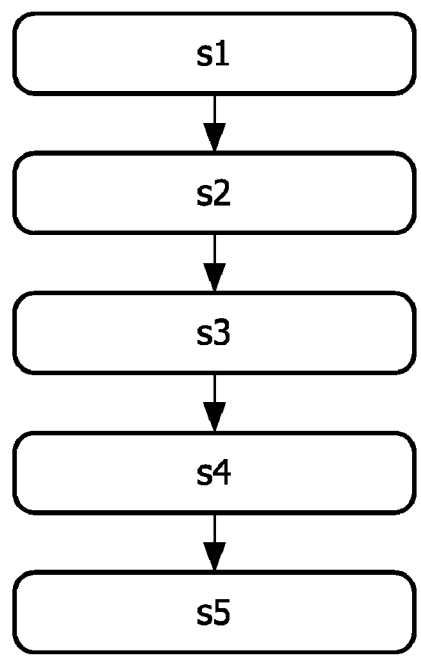
FIG. 8 is a flow chart of a method according to the invention.

FIG. 8 is a flow chart of a method according to the invention. The method enables operating an optical device for assessing optical depth D in a sample 100, the method comprising:

S1 emitting radiation 20 with an initial polarization P_0 with a radiation source 10, S2 arranging a first 30a and a second 30b radiation guide in relation to the sample, the first radiation guide 30a being optically connected to the radiation source for emitting radiation 20 to the sample, the first and the second radiation guide having their respective end portions 30a' and 30b' substantially aligned with each other, the end portions further being arranged for capturing reflected radiation 25a and 25b from the sample, S3 providing a detector 40 in optical connection to the first and the second radiation guide, the detector being arranged for measuring, within an optical subband, an indication of:
- a first polarization P_1 of the reflected radiation 25,
- a second polarization P_2 of the reflected radiation 25, said second polarization P_2 being different from the first polarization P_1, and
- a first and a second intensity I_1 and I_2 of the reflected radiation 25a and 25b in the first 30a and the second 30b radiation guide, respectively, and S4 providing processing means 60 operably connected to the detector, the processing means being adapted to calculate a first (f) and a second (g) spectral function within the optical subband, both spectral functions (f, g) being substantially indicative of single scattering events in the sample:
- the first spectral function (f) being a measure of the difference in polarization between the first P_1 polarization of the reflected radiation 25 and the second P_2 polarization of the reflected radiation 25, and
- the second spectral function (g) being a measure of the difference in intensity between the first and second intensities I_1 and I_2 of the reflected radiation, S5 calculating by the processing means 60 a measure of the correlation C between the first (f) and a second (g) spectral function so as to assess whether the single scattering events originate from substantially the same optical depth D within the sample.

The invention can be implemented in any suitable form including hardware, software, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. An optical device for assessing optical depth in an associated sample, the device comprising:
    a radiation source capable of emitting radiation with an initial polarization;
    a first radiation guide and a second radiation guide, the first radiation guide being optically connected to the radiation source for emitting radiation to the sample, the first radiation guide and the second radiation guide having their respective end portions substantially aligned with each other, the end portions further being arranged for capturing reflected radiation from the sample;
    a detector being optically connected to the first radiation guide and the second radiation guide, the detector being arranged for measuring, within an optical subband, an indication of:
        a first polarization of the reflected radiation,
        a second polarization of the reflected radiation, said second polarization being different from the first polarization, and
        a first intensity and a second intensity of the reflected radiation in the first radiation guide and the second radiation guide, respectively; and
    a processor operably connected to the detector, the processor being adapted to calculate a first spectral function and a second spectral function within the optical subband, the first spectral function and the second spectral function being substantially indicative of single scattering events in the sample, the first spectral function being a measure of the a difference in polarization between the first polarization of the reflected radiation and the second polarization of the reflected radiation, and the second spectral function being a measure of the a difference in intensity between the first intensity and the second intensity of the reflected radiation,
    wherein the processor is further arranged to calculate a measure of a correlation between the first spectral function and the second spectral function so as to assess whether the single scattering events originate from substantially the same optical depth within the sample.

2. The optical device according to claim 1, wherein the first spectral function is a polarized light scattering spectroscopy function.

3. The optical device according to claim 1, wherein the second spectral function is a measure of the differential path length between the first radiation guide and the second radiation guide.

4. The optical device according to claim 1, wherein the detector is arranged for measuring, within the optical subband, the first polarization and the second polarization of the reflected radiation captured by the first radiation guide.

5. The optical device according to claim 1, further comprising a third radiation guide is arranged for transmitting radiation with the initial polarization to the sample, the third radiation guide having an end portion substantially aligned with the end portions of the first radiation guide and the second radiation guide.

6. The optical device according to claim 5, wherein the third radiation guide is arranged for capturing the reflected radiation from the sample, the third radiation guide being optically connected to the detector.

7. The optical device according to claim 5, wherein at least one of the first radiation guide, the second radiation guide and the third radiation guide are optical fibers having a diameter of maximum 200 micrometer.

8. The optical device according to claim 5, wherein at least one of the first radiation guide, the second radiation guide, and the third radiation guide forms part of a catheter.

9. The optical device according to claim 5, wherein at least one of the first radiation guide, the second radiation guide and the third radiation guide are optical fibers having a diameter of maximum 50 micrometer.

10. The optical device according to claim 1, wherein the detector is arranged for measuring the first polarization and the second polarization of the reflected radiation in two substantially orthogonal directions.

11. The optical device according to claim 1, wherein the radiation source is arranged for emitting radiation having the initial polarization linearly polarized in a plane substantially parallel to a polarization plane of the measured first polarization or the measured second polarization.

12. The optical device according to claim 1, wherein the processor is further arranged for determining the correlation for more than one region within the optical subband, the processor being adapted to subsequently select a region of optimum correlation for subsequent optical measurements.

13. The optical device according to claim 1, wherein the processor is further arranged for changing the optical subband in dependency on the calculated correlation.

14. The optical device according to claim 1, further comprising an actuator arranged for changing at least a distance of the respective end portions between the first radiation guide and the second radiation guide in dependency of the correlation.

15. A catheter configured for cooperation with an associated optical device, the catheter comprising:
a first and a second radiation guide, the first radiation guide being optically connectable to a radiation source for emitting radiation to a sample, the first radiation guide and the second radiation guide having their respective end portions substantially aligned with each other, the end portions further being arranged for capturing reflected radiation from the sample,
the associated optical device comprising:
a radiation source capable of emitting radiation with an initial polarization;
a detector being optically connected to the first and the second radiation guides, the detector being arranged for measuring, within an optical subband, an indication of:
a first polarization of the reflected radiation,
a second polarization of the reflected radiation, said second polarization being different from the first polarization, and
a first intensity and a second intensity of the reflected radiation in the first radiation guide and the second radiation guide, respectively; and
a processor operably connected to the detector, the processor being configured to calculate a first spectral function and a second spectral function within the optical subband, the first spectral function and the second spectral function being substantially indicative of single scattering events in the sample, the first spectral function being a measure of the a difference in polarization between the first polarization of the reflected radiation and the second polarization of the reflected radiation, and the second spectral function being a measure of the a difference in intensity between the first intensity and the second intensity of the reflected radiation,
the processor further being arranged to calculate a measure of a correlation between the first spectral function and the second spectral function so as to assess whether the single scattering events originate from substantially a same optical depth within the sample.

16. The catheter according to claim 15, further comprising a third radiation guide is arranged for transmitting radiation with the initial polarization to the sample, the third radiation guide having an end portion substantially aligned with the end portions of the first radiation guide and the second radiation guide.

17. The catheter according to claim 16, wherein the third radiation guide is arranged for capturing the reflected radiation from the sample, the third radiation guide being optically connectable to the detector.

18. The catheter according to claim 16, wherein at least one of the first radiation guide, the second radiation guide and the third radiation guide have polarization conserving properties.

19. A method for operating an optical device for assessing optical depth in a sample, the method comprising the acts of:
emitting radiation with an initial polarization with a radiation source;
arranging a first radiation guide and a second radiation guide in relation to the sample, the first radiation guide being optically connected to the radiation source for emitting radiation to the sample, the first radiation guide and the second radiation guide having their respective end portions substantially aligned with each other, the end portions further being configured for capturing reflected radiation from the sample;
measuring by a detector in optical connection to the first and the second radiation guides, within an optical subband, an indication of:
a first polarization of the reflected radiation,
a second polarization of the reflected radiation, said second polarization being different from the first polarization, and
a first intensity and a second intensity of the reflected radiation in the first radiation guide and the second radiation guide, respectively; and
calculating by a processor operably connected to the detector, a first spectral function and a second spectral function within the optical subband, the first spectral function and the second spectral function being substantially indicative of single scattering events in the sample, the first spectral function being a measure of the a difference in polarization between the first polarization of the reflected radiation and the second polarization of the reflected radiation, and the second spectral function being a measure of the a difference in intensity between the first intensity and the second intensity of the reflected radiation; and
calculating by the processor a measure of a correlation between the first spectral function and the second spectral function so as to assess whether the single scattering events originate from substantially the same optical depth within the sample.

20. A non-transitory computer readable medium embodying computer instructions which, when executed by a processor, configure the processor to perform the method of claim 19.

* * * * *